United States Patent [19]

Rhode, III

[11] Patent Number: 5,302,517

[45] Date of Patent: Apr. 12, 1994

[54] METHOD OF CONTROLLING THE EXPRESSION OF A GENE IN A CELL CULTURE, CELL CULTURE VECTOR USED IN THE METHOD AND METHOD OF MAKING THE VECTOR

[75] Inventor: Solon L. Rhode, III, Omaha, Nebr.

[73] Assignee: The Board of Regents of the University of Nebraska, Lincoln, Nebr.

[21] Appl. No.: 857,100

[22] Filed: Mar. 20, 1992

Related U.S. Application Data

[63] Continuation of Ser. No. 555,773, Jul. 19, 1990, which is a continuation of Ser. No. 63,638, Jun. 16, 1987.

[51] Int. Cl.$^5$ .............. C12P 21/00; C12N 5/00; C12N 15/00
[52] U.S. Cl. .................. 435/69.1; 435/240.2; 435/172.3; 935/11; 935/33; 935/34
[58] Field of Search ............. 435/69.1, 320.1, 240.2, 435/252.3, 317.1, 172.3; 935/34, 70, 33, 11, 111

[56] References Cited

PUBLICATIONS

Tratschin et al., Mol. Cell. Biol. 6:2884–2894 (1986).
Rhode (a), J. Virology 55:886–889 (1985).
Gorman et al., Nucleic Acid Res. 11:7631–7648 (1983).
Sodioski et al., Science 227:171–173 (1985).
Gendelman et al., Proc. Natl. Acad. Sci 83:9759–9763 (1986).
Rhode (b), J. Virology 61:1448–1456 (1987).
Lebovitz et al., J. Virology 58:271–280 (1986).

*Primary Examiner*—Jasemine C. Chambers
*Attorney, Agent, or Firm*—Vincent L. Carney

[57] ABSTRACT

To control the production of a protein product by an animal cell culture, a culture of cells is grown to a density greater than one million cells per milliliter wherein the cells have first and second genes under the control of a single promoter with one of said first and second genes being expressed in an early protein which activates said promoter and the other being expressed in a late protein which is said protein product. A starting material for said culture is introduced into it, whereby said culture begins to replicate said early protein for activating said promoter in a self-stimulating manner to cause the other of said first and second genes express itself in said final product. The gene for the early proteins and the gene for the late proteins are artifically positioned into the same genomic region. The first and second promoters are incorporated in the same transactivation region. The vector material is taken from a parvovirus.

9 Claims, 2 Drawing Sheets

METHOD OF CONTROLLING THE EXPRESSION OF A GENE IN A CELL CULTURE, CELL CULTURE VECTOR USED IN THE METHOD AND METHOD OF MAKING THE VECTOR

RIGHTS IN THE UNITED STATES GOVERNMENT

This invention was made with federal support under the following research grants: NSF Grant DMB 8444778-02 and NIH Grant CA37481-01A2. The United States government has certain rights to this invention.

This application is a continuation of application Ser. No. 07/555,773, filed Jul. 19, 1990, which is a continuation of application Ser. No. 07/063,638, filed Jun. 16, 1987.

BACKGROUND OF THE INVENTION

This invention relates to controlling the production of materials expressed by a gene.

It is known to induce cells to produce high levels of desired proteins. In the prior art methods, this induction is controlled by external factors such as the nature of the cloned gene, the temperature, hormones, the nature and amount of nutrients supplied to the cells and the J-like. Such methods have been described in several publications such as for example, "Large-Scale Cell-Culture in Biotechnology" by W.R. Arathoon and J. R. Birch Science v.232, Jun. 13, 1986, pp. 1390-1395.

The prior art methods have the disadvantages of: (1) providing relatively low production; and (2) not being adequately controllable under some circumstances. Thus, where toxic materials are produced, such as the production of a protein that is toxic to the cell that is producing it, the cell. and other cells may be prematurely destroyed by the level of the toxic material in the culture.

Increases in transcription rate have been observed under several circumstances but have not been adapted to practical use in controlling the expression of a gene to provide desired products more effectively.

One such observation showed that increased transcription occurred by accident and was reported without explanation in "Establishment of a Rat Cell-Line Inducible for the Expression of Human Cytomegalovirus Immediate-Early Gene Products by Protein Synthesis Inhibition" *Journal of Virology*, June, 1986, by Rene Boom et. al., pp. 851-859.

It has also been observed that the tat111 gene product of the retrovirus HIV1 (human immunodeficiency virus 1) has a powerful transactivation expression of genes expressed by the HIVI LTR (long terminal repeat). This observation was described in Rosen, C.A., J.G. Sodroski, and W.A. Haseltine, 1985, "In the human T cell lymphotropic virus type III (HTLV-III/LAV) long terminal repeat", *Cell*, 41:813-823; Sodroski, J.G., C.A. Rosen, F. Wong-Stall, S.Z. Salahuddin, M. Popovic, S. Arya, R.C. Gallo, and W.A. Haseltine, 1985, "Transacting transcriptional regulation of human T-cell leukemia virus type III long terminal repeat", *Science*, 227:171-173. This effect has recently been reported to occur subsequently to transcription and the cis element, tar3, that is required, maps to the region −17/+84 in Rosen, C.A., J.G. Sodroski, W.C. Goh, A.I. Dayton, J. Lippke, and W.A. Haseltine, 1986, "Post-transcriptional regulation accounts for the transactivation of the human T-lymphotropic virus type III", *Nature*, 319:555-559.

SUMMARY OF THE INVENTION

Accordingly, it is an object of the invention to provide a novel technique for inducing the expression of genes.

It is a further object of the invention to provide a novel vector which permits the expression of genes to be efficiently controlled.

It is a still further object of the invention to provide a new DNA vector and technique for using the vector to create cells in which the expression of genes may be efficiently controlled.

In accordance with the above and further objects of the invention, cells are modified to have among their genes, a first gene (hereinafter sometimes referred to as the "tat gene" for transactivator of transcription) which becomes self stimulating when the cell is in the presence of a starting material and a second gene (hereinafter sometimes referred to as a target gene) which expresses itself in a desired product. The first gene expresses itself in a material (TAT) which regulates a promoter for increasing the transcription rate of both the first gene and the second gene so that, upon introduction of a starting material that affects the promoter, a self-stimulating reaction is created in which there is amplification of the TAT protein expressed by the first gene and the protein expressed by the second gene. The second gene within the cell expresses itself in the protein that is the desired product of the process.

The cells of the culture are formed by introducing into a cell genetic material that has one or more copies of a first gene. The introduced genetic material on the cell includes one or more copies of a second gene. A promoter that positively regulates both the first gene and the second gene may be in the cell or may be introduced into the cell. The cell may al-so have introduced into it or already have in it a second promoter activated by a different starting material than the material that activates the first mentioned promoter. The second promotor may express another copy of the gene having the first promoter and hence activate all copies of the first promotor to permit a special starting material to be used. After an adequate culture is prepared, the reaction is triggered by adding the starting material to affect the first promoter or second promoter, if present. With this technique control is obtained over the transcription rate of the RNA for the desired protein.

In one embodiment, a plasmid is constructed to transfer into a cell line the DNA for the first gene, the DNA for the second gene and a promoter controlled by the product synthesized by the first gene, which product controls the transcription rate of both the first and second genes. The cell line is then cultured. When the titer of the cell-line is sufficiently great, the substance which regulates the promoter is introduced, thus initiating a chain reaction causing rapid amplification at two levels and therefore rapid production of the desired end product.

In the preferred embodiment, the plasmid for introducing the first and second genes and the promoter are constructed and may be designated as $P_{38}$ NS1cat and is described in Rhode, S., "Journal of Virology", v. 61, n.5, p. 1448-3.456. It is constructed by combining the proper DNA fragments in a suitable plasmid vector that is capable of entering the cell line as more completely described hereinafter.

The above method of regulating the expression of a gene, the cells incorporating material for such regulation and the technique and vector for incorporating the DNA in the cells to provide it with the ability to be regulated have several advantages, such as: (1) they provide a high ratio of the amount of protein in the induced state compared to the noninduced state; and (2) they control the time of expression of the gene. The latter advantage is especially significant where the cells produce a substance which is toxic to the cells.

SUMMARY OF THE DRAWINGS

The above-noted and other features of the invention will be better understood with reference to the accompanying drawings in which.

DETAILED DESCRIPTION

Figure 1:
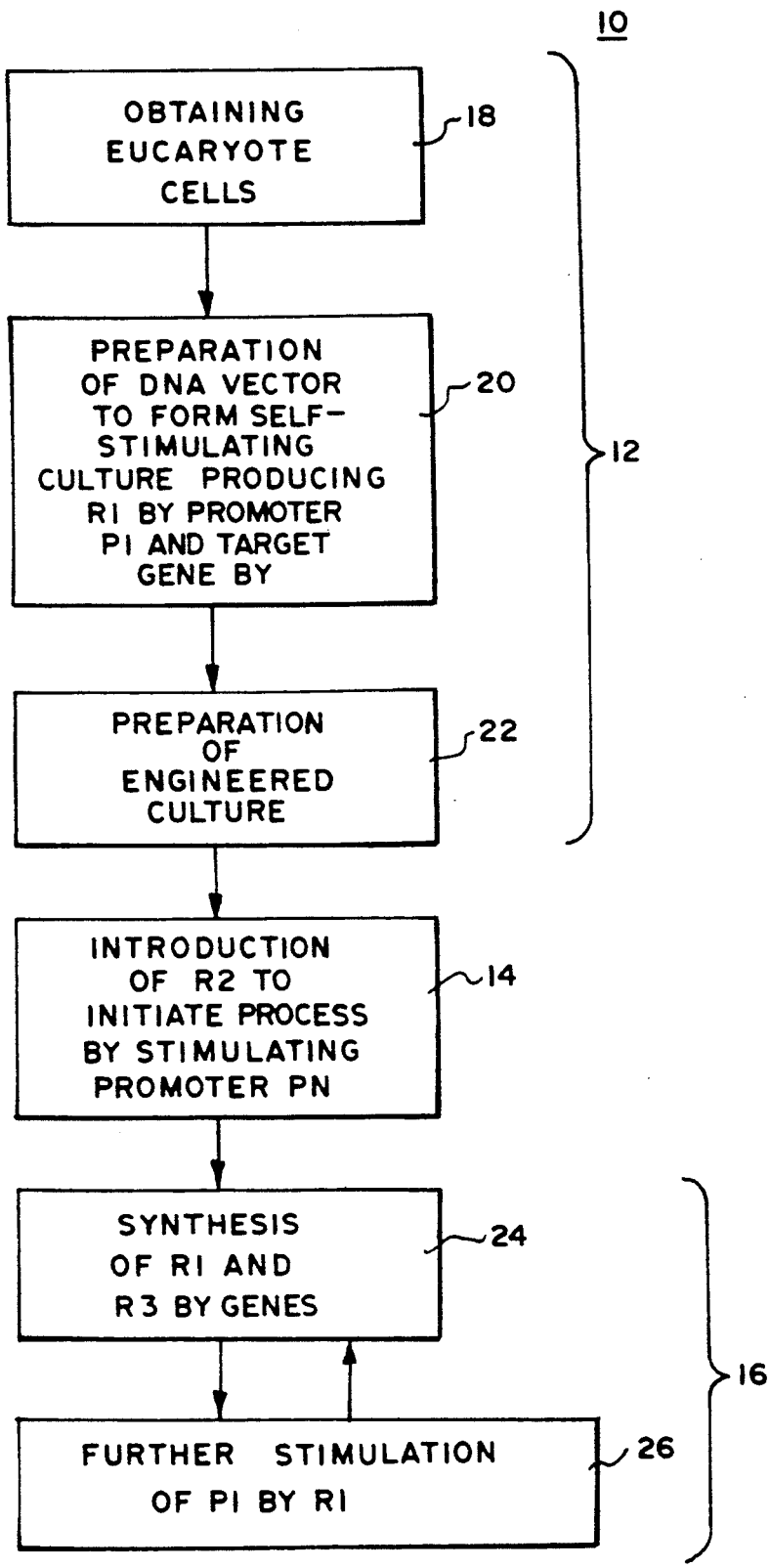
FIG. 1 is a block diagram illustrating the technique of this invention.

In FIG. 1, there is shown a block diagram of a process 10 for practicing the invention including a subprocess 12 for preparing a culture which contains within it a gene which, when expressed, results in a substance that promotes further expression of the gene along with expression of other genes so as to have a self-stimulating effect, a step 14 of introducing the substance which stimulates expression of the gene to initiate the process and the subprocess 16 which involves the generation by expression of the first gene of the promoter causing amplification of expression and the expression of other genes resulting in a desirable material which is later removed.

The subprocess of preparing a culture which is self-stimulating includes the step 18 of obtaining eucaryote cells, the step 20 of preparing a DNA vector to form a self-stimulating expression of an end product, R1, and the step 22 using the DNA vector and the eucaryote cells to prepare the engineered culture, which when stimulated by a starter substance, amplifies production of the final product in a self stimulating process.

Several cell cultures have been found to be suitable for receiving the necessary DNA to have the desired self-stimulating action as will be described more fully in the examples. For example, certain known cell lines indicated by NB, Rela Gey and HeLa S3, are suitable cell lines.

A suitable DNA vector containing a target gene is a designed plasmid p2VP constructed by ligating the Hind 111/Bam H1 fragment from the genomic clone of the parvovirus H1 TS6 which contains the coat protein region to the Hind 111/Bam H1 restricted plasmid ptar2cat2. However, other vectors may be constructed.

The vector must be capable of carrying into the cells for expression therein, sufficient genetic material so that a starting material energizes a promoter which regulates at least a first gene and a second gene. The first gene expresses itself in a material that increases its rate of transcription and the second gene expresses itself in the desired end product. The first material may be a viral early protein that positively regulates a second gene, and the second material which is the final product may be a viral late protein or some other protein of value.

In this specification, early and late proteins means that the early protein appears earlier and the second protein appears later without regard to whether they can be shown to be produced in early or late stages of viral replicative cycles using metabolic inhibitors of DNA synthesis but does mean the early protein must appear before there is substantial synthesis of the late protein in the same genomic region.

The subprocess 16 includes the steps 24 of synthesizing the final product, R3, and a substance, R1, that stimulates the promoter PI and the step 26 of further stimulating systhesis. The final product, R3, is a late protein. The other substance, R1, is an early protein. The step 26 includes the stimulation of P1 by R1 and thus further stimulating synthesis of R1 and R2 to form a closed loop which accelerates the synthesis of the final product, R3.

More generally, genetic engineering is used to create a genetic switch that has as its central component, a gene that positively regulates other cloned genes through a specific DNA target sequence (tar or transactivation responsive element). The switch is generated by using the tar element to regulate the RNA synthesis for the protein that acts upon the tar. Thus, a "self-stimulatory" loop is established.

In one embodiment of cell culture and one embodiment of vector used to create the cells in the cell culture, the parvovirus protein NSI is the positive regulator of the $P_{38}$ promoter, which contains the NS1 tar element. Other genes placed in the cell are also "turned on" by NS1 when they are placed under the control of $P_{38}$.

This system allows high level expression of cloned genes in animal cells with resultant production of large amounts of specific proteins of commercial or research interest. The high level production occurs only after an inductive signal and not during routine preparation of the cells and their propagation. This makes it more efficient to produce proteins that are toxic to the cells making them.

This process may be used for production of vaccines, peptide hormones and growth factors, and other protein biologicals such as anticancer proteins, especially those that require modification by the cell after their initial synthesis. The actual techniques of large scale production are not part of this invention except insofar as they cooperate with the genetic switch of this invention. Some such techniques are disclosed in the aforementioned publication to Arathoon et. al., the disclosure of which is incorporated herein.

Figure 2:
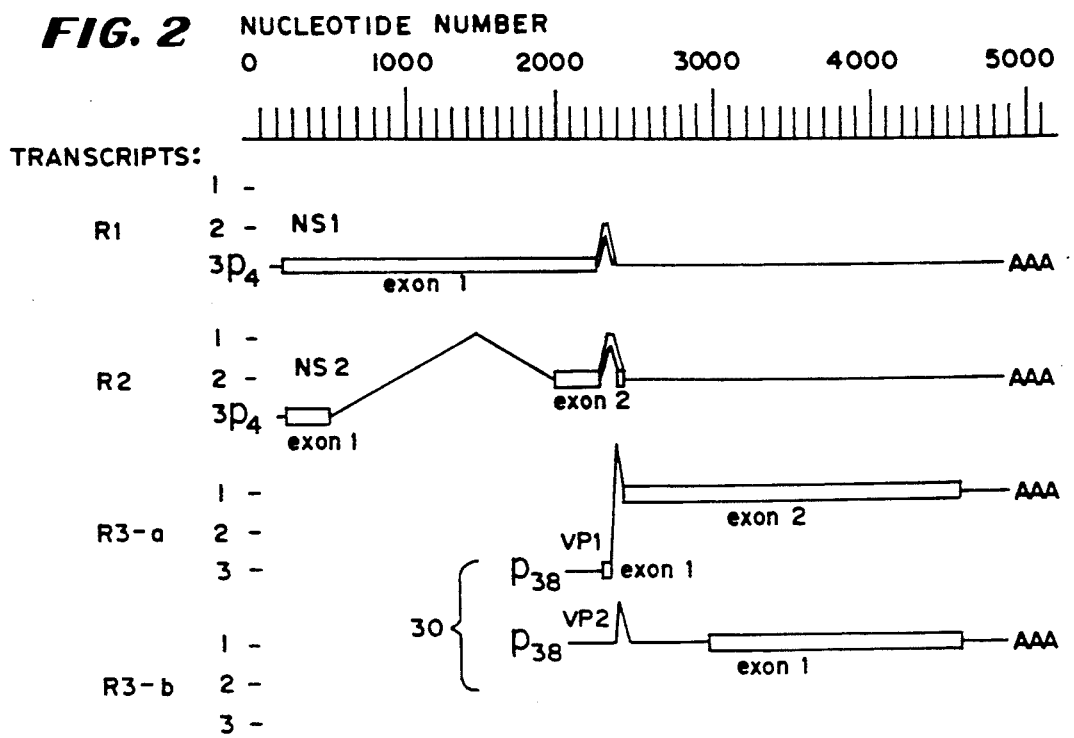
FIG. 2 is a genetic map of a portion of a virus used in accordance with the invention.

In FIG. 2, there is shown a genetic map showing the genomic region of the parvovirus HIV1. As shown in this figure, a promoter $P_{38}$ indicated at 30 from the parvovirus regulates two capsid proteins shown at VP1 and VP2 and has the protein NS1 as an inducing substrate, the promoter of which is $P_4$ in the parvovirus. The genes NS1 and NS2 are superimposed (in the same region and overlap) and they are regulated by the same promoter. In the Preferred embodiment, the arrangement of the virus is modified by replacing the promoter $P_4$ with the promoter $P_{38}$. The inducing material may be a substrate for an inhibiting gene or any other mechanism for inducing the activity of the promoter which induces activity of the inducing material.

To prepare the stable cell line, at least some of the DNA necessary to establish the auto stimulating sequence is supplied by a DNA vector. The DNA must integrate within the cell. in such a manner that the promoter and the first and second genes are in the same region. in the preferred embodiment the $P_{38}$ promoters in the plasmid and the two genes involved are in the same genomic region.

Figure 3:
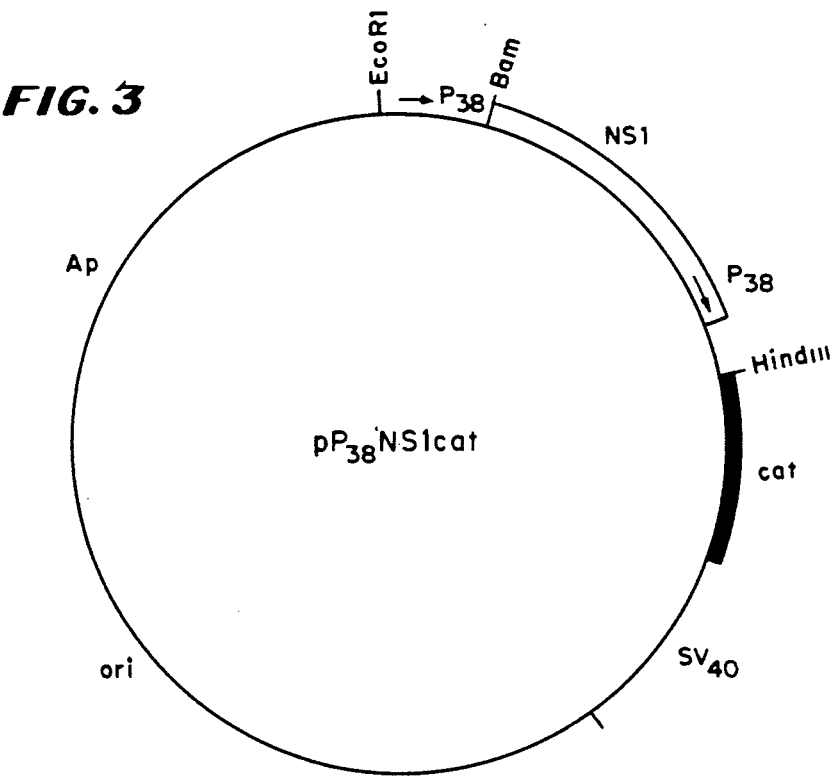
FIG. 3 is a diagram of a plasmid $pP_{38}NS1$-cat used as a vector in accordance with the invention.

In FIG. 3, there is shown a plasmid constructed from parvovirus DNA of FIG. 2 to contain a promoter and a gene in close proximity to each other, with the gene which includes the promoter $P_{38}$ as a constituent part for itself and a target gene for expression of cat (chloramphenicol acetyl transferase). Other genes may be used as the target gene to express proteins other than cat in a manner known in the art.

This plasmid, when integrated into eucaryotic cells, produces a protein expressed by another gene, which in FIG. 2, is the cat gene (chloramphenicol. acetyl transferase gene). In the example, NS1 is from a selected parvovirus and cat is a reporter indicator gene used to test expression.

EXAMPLES

The following non-limitative examples illustrate the invention.

GENERAL

A plasmid was constructed as a DNA vector to provide two genes which are positively regulated by the same (copy) promoter in certain cell lines, with one protein expressed by one of the genes stimulating the promoter and the other protein expressed by the other gene being the end product desired. The DNA vector was used to engineer three different human cell lines and the results were tested. The procedures are described in the aforementioned publication by Solon L. Rhode III, "Construction of a Genetic Switch for Inducible trans-Activation of Gene Expression in Eucaroyotic Cells", *J. Virol*, May 1987, n.5, v. 61, p. 1448-1486, the disclosure of which is incorporated herein.

SOURCE OF MATERIALS

The Hela Gey cell line was obtained from the American Type Culture Collection, Rockville, Md., where it is designated as No. CCL2.1. The Hela S3 cells were obtained from the American Type Culture Collection, Rockville, Md., where it is designated as No. CCL2.2.

PREPARED MATERIALS

The $SV_{40}$ transformed human kidney cell line NB may be obtained as described by Shein, H.M. and J.P. Enders, 1962, "Multiplication and cytopathogenicity of simian vacuolating virus 40 in cultures of human tissues". *Proc. Soc. Exp. Biol. Med.*, 109:495, the disclosure of which is incorporated herein by reference. They are available from a culture designated as EPP2, internal Epply Number EPP2 (collection of Eppley Cancer Institute, University of Nebraska Medical Center, 42nd and Dewey Avenue, Omaha, Nebr. 68105-1065).

The plasmid $pP_{38}$ NS1cat was constructed by cloning the parvovirus H-1 $P_{38}$ promoter region in the DNA fragment ECORI/Pst1 (map positions 21/42) into the plasmid pUC8. The Hind111 site was restricted, filled in with T4 polymerase and BamRI linkers were added. This plasmid is available from a culture designated as EPP1, internal. Epply Number EPP1 (collection of Eppley Cancer Institute, University of Nebraska Medical Center, 42nd and Dewey Avenue, Omaha, Nebr. 68105-1065).

After restricting with BamH1, the plasmid was religated and recovered by transfection. This converted the Hind111 site to a BamH1 site at the +127 (relative to the cap site) position of the $P_{38}$ promoter. The region −108 to +127 was recovered from this construction by restricting with Ncol/BamH1 and inserted into a pBR327 recombinant containing the NS1 gene (pH5Cat) that hac1 been deleted from the BamH1 linker at the 5' end to the Mbol site at nucleotide 1862 (−146 relative to the $P_{38}$ promoter cap site) as described in Rhode, S.L. III, 1985, "Trans-activation of parvovirus $P_{38}$ promoter by the 76K noncapsid protein", *J. Virol.*, 55:886-889 the disclosure of which is incorporated herein. This step positioned the PBR327 ClaI site at the 5' side of the $P_{38}$ promoter, destroyed the BamH1 site that was at the left end of the genomic clone and retained the BamH1 site at the +127 position.

A BamH1 site was positioned at the start of the NS1 gene by first isolating the beginning of the gene from nucleotides 0 to 1,250. This was done by deleting the plasmid pH5cat that contains the complete H-1 genomic sequences from approximately 0 to the Hind111 site at 2,655 fused to the cat gene of all the H-1 sequences and cat sequences between the Bg111 at nucleotide 1,250 and the BamH1 site after the $SV_{40}$ processing signals. This rendered the NcoI site at the ATG start codon of NS1 a unique site. The NcoI site was filled in with the T4 polymerase, and BamH1 linkers added. The $P_4$ promoter was excised from the resulting plasmid with Cla1/BamH1 and the Cla1/BamH1 fragment that contains the $P_{38}$ promoter was ligated into its place. The $P_{38}$ fusion to the 5' portion of the NS1 gene was excised with Cla1/Acc1 (Acc1 is at nucleotide 1016) and ligated to a pH5cat plasmid which had its BamH1 site previously destroyed. The resulting plasmid was $PP_{38}$ NS1cat.

The plasmid PMNS1 cat was constructed by removing the $P_{38}$ promoter in front of NS1 in $pP_{38}$ NS1cat with Cla1/BamH1 and inserting the MMTV promoter from the plasmid PM14-1 using the method described in ostrowski, M.C., A.L. Huang, M. Kessel, R.G. Wolford, and G.L. Hager, 1984, "Modulation of enhancer activity by the hormone responsive regulatory element from mouse mammary tumor virus", *The EMBO J.*, 3:1891-1899 as a Clal./BamH1 fragment. This plasmid is available in the culture designated EPP3, internal Epply Number EPP3 (collection of Eppley Cancer Institute, University of Nebraska Medical Center, 42nd and Dewey Avenue, Omaha, Nebr. 68105-1065).

The plasmid PHMNS1 cat was constructed by inserting the Harvey Sarcoma enhancer from the plasmid pM14-1 as a Cla1 fragment into the Cla1 site of pMNS1cat. This plasmid is available in the culture designated EPP4, internal Epply Number EPP4 (collection of Eppley Cancer Institute, University of Nebraska Medical Center, 42nd and Dewey Avenue, Omaha, Nebr. 68105-1065).

The plasmid p2VP was constructed by ligating the Hind111/BamH1 fragment from the genomic clone of H-1 ts6 which contains the coat protein region to the Hind111/BamH1 restricted plasmid ptar2cat2. Briefly, this plasmid has a tandem repeat of the $P_{38}$ promoter with the 5' copy including sequences from −146 to +8 and the second copy from −146 to +648 (Hind111 site of H-1 at nucleotide 2,655). The ptar2cat2 has a low constitutive expression of cat and a high transactivation by NSI. The plasmid is available from the culture designated EPP5, internal Epply Number EPP5 (collection of Eppley Cancer Institute, University of Nebraska Medical Center, 42nd and Dewey Avenue, Omaha, Nebr. 68105-1065). Synthetic oligonucleotides were produced on an Applied Biosystems 380B DNA synthesizer by standard methods.

DNA TRANSECTION

Calcium phosphate precipitates of plasmid DNA and carrier calf thymus DNA were added to 60 mm (millimeter) dishes of cells in a volume of 0.5 ml (milliliter). The cultures were treated with 15 percent glycerol in Hepes buffer for 4 minutes at 4 hours after transfection and the cultures were subsequently treated with Na Butyrate for 16 hours as previously.

Cotransfections were carried out with either of the selectable marker genes: (1) aminoglycoside phosphotransferase (neo) in the plasmid pSV2neo using the methods described by Wigler, A. Perlerer, S. Silverstein, R. Axel, G. Urlecut, and L. Chasin 1979 "Biochemical transfer of a single copy eukaryotec genes using total cellular DNA as donor", *Proc. Natl. Acad, Sci. USA*, 76:1373–1376 or (2) guanine phosphoribosyltransferase (gpt) in the plasmid pSV2gpt as described in Mulligan, R. and P. Berg, 1981, "Selection for animal cells that express the Escherichia coi gene coding for exanthimeguanine phosophoribosyltransferase", *Proc. Natl. Acad. Sci. USA,* 78:2072–2076.

NB cells were selected for neo gene expression by exposure to G418 at 1 mg/ml and Hela cells were treated with 1.5 mg/ml. The selections for gpt were as described in the aforementioned publication, Mulligan, R. and P. Berg, 1981, "Selection for animal cells that express the Escherichia coi gene coding for exanthimeguanine phosophoribosyltransferase", *Proc. Natl. Acad. Sci. USA,* 78:2072–2076. The selections for the herpes thymidine kinase (tk) gene were in medium containing 0.5 ug/ml. methotrexate, 10-5 M thymidine, nonessential amino acids as a source of glycine, and 13 ug/ml. adenine applied 48 hours after transfection.

TEST PROCEDURES

Transient Expression Assays

The activity of the indicator gene choramphenicol acetyl transferase (cat) was assayed as previously described. Samples with high activity were diluted until no more than 60 percent of the substrate was acetylated.

Immunoflourescent staining

Cells were plated on glass coverslips in 35 mm petri dishes and at the proper time washed with Hank's balanced salts and fixed with cold acetone for capsid antigen staining and with 2.5 percent paraformaldehyde for 15 minutes at room temperature for NS1 staining. Dried and fixed cells were stored at −20C until stained. Capsid antigens were detected using anti-H-1 antisera from hamsters that had survived a neonatal infection with H-1. The NSI specific antibody was obtained by immunization of rabbits with an NS1 fragment fusion protein. The primary antibody was detected by indirect immunoflourescence using the biotin/avoiding reagents obtained from Vector Laboratory in Burlingame, Calif.

EXAMPLE 1

A plasmid was first constructed in which the tk gene was positioned to be transactivated by NS1, pH5tk, and this construction was inefficient at producing tk+colonies. All of these results, whether the NS1/NS2 gene was in trans or in cis to the marker gene, suggested that the NS1/NS2 gene was toxic and reduced the yield of stable transformants after transfection with a number of dominant selectable marker genes.

EXAMPLE 2

Transient Expression of $P_{38}$ NS1cat

To circumvent the possible toxicity of $P_4$ driven NS1/NS2, the plasmid $pP_{38}$ NS1cat shown in FIG. 3 was constructed. This construct places NS1/NS2 under the low constitutive expression of $P_{38}$, but in the presence of threshold amounts of NS1, the transactivation of the $P_{38}$ promoters provide an autostimulatory expression of NS1/NS2 as well as the cat gene.

In transient assays in NB cells, $pP_{38}$ NS1cat showed a high level of expression, though not as high as pH5cat. As a test for the presence of competent cells that have taken up $pP_{38}$NS1cat but have not expressed it, additional NS1 was made available to trigger the positive feedback loop of $PP_{38}$NS1cat by cotransfection with pH5, a plasmid that expresses NS1 under the $P_4$ promoter.

There was some increase in cat expression in the presence of pH5. In another experiment, the responses of $pP_{38}$ NS1cat, pH5cat (p4cat with NS1 under the $P_4$ promoter), and PmNS1cat NS1 under the MMTV promoter) are compared when they were transfected alone or in the presence of a NS1 producing plasmid, PH5, or in the presence of additional indicator plasmid, pH3cat. The pH3cat has the cat gene fused to the $P_{38}$ promoter but does not produce NS1 or NS2.

In this experiment, the $P_4$ driven NS1 construction showed a decrease in cat expression when additional NS1 plasmid was included and an increase in cat when additional $P_{38}$ cat was included. This increase was too large to be accounted for by the constitutive level of $P_{38}$ cat. This result suggests that the $P_4$ driven NS1. gene produces a level of NS1 that saturates the $P_{38}$ cat gene that is present in stoicometric amounts. Additional NS1 represses rather than stimulates $P_{38}$ further. In contrast, the $P_{38}$NS1cat plasmid was stimulated by cotransfection with pH5 (i.e., NS1). Additional $P_{38}$cat also increased the total expression of cat.

The result is believed to occur because additional NS1 activates expression in some cells that would otherwise have only constitutive levels of cat, and additional $P_{38}$cat increased the yield of CAT enzyme because in those cells that have transactivating levels of NS1, it is produced in excess. The MMTV promoter is relatively weak, therefore, NS1 is probably not produced in saturating amounts with pMNS1cat. Thus, an increase in cat with the addition of pH5 to PMNS1 cat was expected. The decreased yield with PMNS1 cat and additional $P_{38}$ cat was surprising and reproducible.

EXAMPLE 3

Stable Cell lines Containing $pP_{38}$NS1cat

The NB cell line that is permissive for H-1 infection and used for plaque titrations was cotransfected with 1 ug of pSV2neo and 4.5 ug of $pP_{38}$NS1cat per 60 mm dish. The yield of colonies was 12 and 13 for two such dishes as compared to 31 in a dish transfected with pSV2neo in the absence of $pP_{38}$NS1cat. Five G418 colonies were grown to mass culture and tested for cat expression with and without infection with H-1 20 hours prior to the cell extraction. Four out of the five clones had some expression of cat, two clones had very low levels and were not inducible on superinfection with virus and two had at least a 10 fold increase in cat with infection.

One of these, NBA6, was chosen for further study. This cell line is available in the culture designated EPP6, internal Eppley Number EPP6 (collection of Eppley Cancer Institute, University of Nebraska Medical Center, 42nd and Dewey Avenue, Omaha, Nebr. 68105-1065). The cell line was screened with various treatments to determine what could induce an increased cat expression. Infection with the parvoviruses H-1, minute virus of mice (MVM), and canine parvovirus (CPV) induced strong responses. Treatment of the cultures with 5-azacytidine at 5 uM for 24 hours followed by a 24 hour chase failed to stimulate cat expression. Sodium butyrate at 2.5 mM for 16 hours followed by a chase of 24 hours induced increased expression while 16 hours of sodium butyrate immediately before extraction was not effective.

In a similar experiment, retinoic acid at 10-6 or 10-7 M was not active. A 4-hour treatment with the inhibitor of protein synthesis cycloheximide followed by a chase of 40 hours produced a 5-fold stimulation that was not studied further. The tumor promoter TPA was tested at various doses and was found to produce some induction at toxic levels of 20 ng/ml for 8 hours followed by a chase period of 40 hours. The combination of sodium butyrate and TPA was more active than either alone. Twenty-four hour treatments with TPA produced significant cell toxicity at all levels greater than 0.1 ng/ml. The standard induction treatment chosen to achieve the highest response with minimal toxicity was 5 mM sodium butyrate and 0.1 ng/ml of TPA for 24 hours. Sodium propionate at 5 mM also induced cat expression but was not as potent as butyrate.

The kinetics of the response were tested with replicate cultures treated with sodium butyrate and TPA and then chased for various times. The cultures that were followed beyond 5 days were trypsinized at day 3 and transferred to a T25 flask and subcultured to a 60 mm dish 24 hours prior to extraction. The final yield of enzyme was corrected for the cell dilution of subculturing assuming a 100 percent plating efficiency. The induction of cat expression is slow to occur and very little increase is seen until about 36 hours after the start of the induction. The levels of cat then rise rapidly to a peak at about day 3, and in this experiment, the induced level reached 550 fold higher than the constitutive level. The yield of enzymes then gradually falls back to the constitutive level over a period of 4 to 5 days. A repeat induction produces a second response equal to the first.

EXAMPLE 4

Similar transfections were made of PP$_{38}$NS1cat into Hela Gey monolayer cells and Hela S3 cells and isolated clones screened for inducibility with sodium butyrate treatments. For Hela S3, 4 out of 12 clones had inducibile cat expression, and the remaining had no detectable level of cat. For Tlela Gey, 4 of 6 clones had inducible enzymes, one had no detectable cat, and one had a weak constitutive expression that was not inducible.

The inducible clones varied in their constitutive levels of enzyme and the response to induction. The most responsive clones increased their cat expression by greater than 20 fold at 48 hours after the start of induction. The kinetics of response of one Hela Gey clone, G3 was determined. This cell line is available in the culture designated EPP7, internal Epply Number EPP7 (collection of Eppley Cancer Institute, University of Nebraska Medical Center, 42nd and Dewey Avenue, Omaha, Nebr. 68105-1065). This clone did not induce as high a level as NBA6, reaching 100 fold, and was slower to return to baseline. Otherwise, the response was very similar.

EXAMPLE 5

Demonstration of the Induction of NS1

In our initial experiments, pooled anti-H-1 antisera was used from hamsters that survived neonatal infection with H-1 for immunoflourescent and immunoprecipitation assays for NS1. The results with the immunoflourescent staining were that induced cultures showed some cells with weakly positive nuclei not seen in uninduced cultures or in induced cultures stained with nonimmune sera.

The immunoprecipitations of labeled proteins from induced cultures failed to detect NS1. NS1 was demonstrated in H-1 infected cultures at 18 hours post-infection and was at the same level in infected NB cells as in infected NBA6.

To demonstrate NS1 more convincingly, the NS1 specific antibody was obtained and used in an assay. Positive cells were very rare on the non-induced control with only 5 found on the whole coverslip at 48 hours. The induced coverslips reached an apparent high of 10 percent positive cells for NS1. at 48 hours post-induction. The induced cultures showed some toxicity to the induction in this experiment and some cells were lost from the coverslip.

It is not known whether the cells that were lost were induced to express NS1 or not. In the infected cells that were lightly stained for NS1, there is an apparant pattern of localization visible within the nucleus superimposed on a more generalized lightly stained background. The increase in cat activity of 100–500 fold with induction seems to roughly correlate with the increase in cells staining positively for NS1. This result suggests that the constitutive level of cat expression can be accounted for by a low rate of cells that spontaneously induce high levels of NS1 expression.

EXAMPLE 6

Inductible Expression of the H-1 Coat Protein Gene

As a test of the capacity of the inducible NS1/NS2 cassette to transactivate other genes directed by a P$_{38}$ promoter when introduced into the cell, clones of NBA6 transfected with p2VP were examined. This plasmid has a tandem duplication of the P$_{38}$ promoter that displays a low constitutive expression level and a strong response to transactivation by NS1 when fused to the cat gene.

In this construct, the promoters are fused to the coat protein gene of the H-1 temperature sensitive mutant ts6, which was subcloned from the genomic clone pSR1. In transient expression, assays examined by immunoflourescence, the plasmid produces globular nuclear antigen with an appearance identical to that after infection with the mutants ts1 or ts6 as described in Rhode, S.L. III, 1976, "Replication Process of the Parvovirus FT-1 V. Isolation and characterization of temperature-sensitive H-1 mutants defective in progeny DNA synthesis", *J. Virol.*, 17:659–667 or ts6.

Stable transformants were produced by cotransfection of NBA6 with pSV2gpt and p2VP. When cultures were treated with I ug of pSV2gpt and 10 ug of p2VP, the yield of colonies was reduced by 70 percent, and ½ ug of pSV2gpt and 15 ug of −2VP gave no colonies. A total of 8 clones were expanded to mass culture and tested by immunoflourescence for H-1 antigens after induction with Na butyrate. Two clones showed definite positive nuclei with the characteristic pattern of ts6 and 3 showed rare cells with a ts6 pattern of nuclei. One clone NBA6/p2VP1 was selected for further study.

This clone illustrates the immunoflourescence staining of NBA6/p2VP1 with and without the sodium butyrate induction. The percentage of positive cells is low, about 10 percent at 48 hours after induction. The appearance of the cells suggests that the level of antigen produced in the positive cells approaches that produced by infection with ts 6. This result establishes that additional genes driven by the $P_{38}$ promoter can be introduced as stable integrates into cells with an inducible transactivation expression and be coordinately regulated by NS1.

EXAMPLE 7

Improvement in the induction Efficiency

To maximize the capability of this inducible expression system to produce protein from cloned genes, an increase in the efficiency of induction from the current level of about 10-20 percent is needed. One approach is to introduce the NS1 gene into cells with two types of inducible promoters, one that responds to a direct signal and the second which responds to the autostimulatory NS1 induction ($pP_{38}NS1cat$). The glucocorticoid inducible promoter from the retrovirus mouse mammary tumor virus (MMTV), was first used but in NB and Hela cells, this promoter did not express NS1 at high enough levels to induce $pP_{38}NS1cat$ in transient assays. Therefore, the Harvey sarcoma enhancer fragment was added on the 5' side of the MMTV enhancer as in the plasmid of pM14-1 described by Ostrowski, et al (Ostrowski, M.C., A.L. Huang, M. Kessel, R.G. Wolford, and G.L. Hager, 1984, "Modulation of enhancer activity by the hormone responsive regulatory element from mouse mammary tumor virus", *The EMBO J.*, 3:1891-1899). This plasmid, pHMNS1cat, has a low level of cat expression in transient assays and responds well to dexamethasone stimulation. The behaviour of pHMNSicat in the transient assay suggests that it might be suitable as a trigger mechanism to induce $pP_{38}NS1cat$.

As an initial test, Hela S3B1 cells, a clone that contains a sodium butyrate or superinfection inducible $pP_{38}NS1cat$, were cotransfected with pSVC2gpt and pHMNS1cat. A total number of 7 clones were isolated by selection for gpt expression, expanded to mass culture, and tested for inducibility with dexamethasone. One of the 7 clones was induced by dexamethasone, and this clone, Hela S3B1D1 was selected for further study. This culture is available under the designation EPP8, internal Epply Number EPP8 (collection of Eppley Cancer Institute, University of Nebraska Medical Center, 42nd and Dewey Avenue, Omaha, Nebr. 68105-1065).

EXAMPLE 8

In order to conserve selectable marker genes for the introduction of the final target genes for expression into cell lines with inducible transactivation, experiments were performed to see if the glucocorticoid responsive NS1 plasmid and $pP_{38}NS1cat$ could be introduced into cells in one step. Hela Gey and Hela S3 cultures were transfected with the selectable marker genes pSV2neo or pSV2gpt and a mixture of pHMNS1cat and $PP_{38}NS1cat$. The resulting clones were screened for the inducibility of high levels of cat expression with dexamethasone alone. This experiment is incomplete.

The effect of increased transcription in some applications has recently been reported to occur subsequently to transcription and the cis element, tar3, that is required, maps to the region −17/+84. This was reported in Rosen, C.A., i.G. Sodroski, W.C. Goh, A.T. Dayton, J. Lippke, and W.A. Haseltine, 1986, "Post-transcriptional regulation accounts for the trans-activation of the human T-lymphotropic virus type III", *Nature*, 319:555-559).

Since the transactivation is after transcription, the active sequences in tar3 are probably between +1 and +84. Inspection of the sequence of tar 3 reveals a prominent tandem repeat. To test this hypothesis a modified tar3 with synthetic oligonucleotides was prepared. This truncated tar3 was cloned into a position just near the TATA box of $P_{38}$ and fused to the cat gene at the Hind111 site. This plasmid, $PP_{38}cattar3$, was tested in a transient assay with an NS1 producing plasmid and with and without cotransfection with a plasmid containing the tat111 gene expressed by the RSV promoter, PRSVtat111-1.

The results indicated that the synthetic tar3 element responded to the tat111 transactivation, but the expression was low and not as great as the $P_{38}$ plasmid prior to the insertion of the tar3. This implies that the tat111-/tar3 transactivation system can be coupled to the inducible transactivation of transcription to enhance the expression of the final target gene, but other promoters, such as the HIV LTR or modified versions of it may be superior to $P_{38}$ in this application.

The above method of regulating the expression of a gene, the cells incorporating material for such regulation and the technique and vector for incorporating the DNA in the cells to provide it with the ability to be regulated have several advantages, such as: (1) it provides a high ratio of induced protein to inducing substance; and (2) it controls the time of expression of the gene. The latter advantage is especially significant where the cells produce a substance which is toxic to the cells.

What is claimed is:

1. A method of controlling the expression of a protein product in a mammalian cell culture comprising the steps of:
    growing a culture of mammalian cells to a density in the range of 100,000 to 10 million cells per millilier, wherein said cells have been transfected with DNA comprising first and second genes each under the control of the parvovirus $P_{38}$ promoter, and wherein one of said first and second genes expressing an early protein which activates said $P_{38}$ promoter and the other expressing a late protein which is said protein product, and
    introducing into said culture sodium butyrate to activate said $P_{38}$ promoter, whereby the cells in said culture begin to express said early protein for activating said $P_{38}$ promoter in a self-stimulating manner to cause the other of said first and second genes to express the late protein.

2. A method in accordance with claim 1 of cells, wherein the second gene expresses a late protein selected for commercial value.

3. A method in accordance with claim 1 further including the steps of testing for infectious virus and introducing sodium butyrate only in the absence of said infectious virus.

4. A method in accordance with claim 3 wherein said first gene for the early protein and said second gene for the late protein are artifically positioned into the same genomic region.

5. A method according to claim 4 prior to the introduction of sodium butyrate wherein said early protein is not expressed by said cells.

6. A method in accordance with claim 2 in which the step of growing a culture includes the step of preparing a plasmid with parvovirus $P_{38}$ and a first and second gene regulated by the promoter, with one of said first and second genes producing the early protein which regulates the promoter and injecting the DNA from the plasmid into a mammalian cell line.

7. A method in accordance with claim 6 wherein said step of preparing a plasmid comprises substeps of obtaining a material capable of serving as a vector with a genomic region having early and late proteins wherein an early protein activates the promoter for the late proteins; and inserting the genomic region containing the genes for the early and late proteins and their respective promoters into an animal cell line.

8. A method according to claim 7 in which said vector material is modified so that the genes for said early and said late proteins are in the same region controlled by said promoter, whereby said vector may induce in mammalian cell lines the ability to synthesize the desired protein product upon the presence only of the first protein.

9. A method according to claim 8 further including the step of removing from said vector material the promoter for the first gene and retaining in the vector material the promoter for the gene that expresses itself in the late protein which promoter is activated by the early protein.

* * * * *